United States Patent [19]
Young et al.

[11] Patent Number: 4,915,098
[45] Date of Patent: Apr. 10, 1990

[54] ORTHOPAEDIC HINGE MECHANISM

[75] Inventors: David E. Young, Oxfordshire; Kenneth P. Davis, Hillingdon, both of England

[73] Assignee: Protectair Limited, Abingdon, England

[21] Appl. No.: 34,023

[22] Filed: Apr. 3, 1987

Related U.S. Application Data

[63] Continuation-in-part of Ser. No. 853,962, Apr. 21, 1986, abandoned.

[51] Int. Cl.[4] ............................................. A61F 3/00
[52] U.S. Cl. ................................... 128/88; 128/80 C; 128/80 F
[58] Field of Search .................. 128/80 C, 88, 80 F

[56] References Cited

U.S. PATENT DOCUMENTS

| | | | |
|---|---|---|---|
| 2,573,866 | 11/1951 | Murphy | 128/80 F |
| 4,245,629 | 1/1981 | Cumming | 128/80 C |
| 4,337,764 | 7/1982 | Lerman | 128/80 |
| 4,361,142 | 11/1982 | Lewis | 128/80 C |
| 4,493,316 | 1/1985 | Reed | 128/80 C |
| 4,502,472 | 3/1985 | Pansiera | 128/80 F |
| 4,524,764 | 6/1985 | Miller et al. | 128/80 C |
| 4,599,998 | 7/1986 | Castillo | 128/80 C |
| 4,655,201 | 4/1987 | Pirmantgen | 128/80 C |
| 4,657,000 | 4/1987 | Hepburn | 128/88 |

OTHER PUBLICATIONS

Published EP Appl. 0 059 472, published 9/8/82.
Rolyan Medical Products, Catalog, 1986, coversheet and p. 24.
Published UK Appl. GB 2,163,352A, published 2/26/86.
Published PCT Appl. WO82/02658, published 8/19/82.
Published UK Appl. GB 2,168,106A, published 6/11/86.

Primary Examiner—William Pieprz
Assistant Examiner—Huong Q. Pham
Attorney, Agent, or Firm—Tilton, Fallon, Lungmus & Chestnut

[57] ABSTRACT

An orthopaedic hinge mechanism has a body with at least one pivot and at least one hinge arm mounted thereon and having two cam abutment stops which arise from the said hinge arm either side of and close to the pivot.

Screw adjustment means are housed in threaded holes in the hinge body in the plane of the hinge arms and may be driven down to impinge on the cam abutment stops. The plane of the operating surfaces of the cam abutment stops is at right angles to the axis of the motion limiting screws. The mechanism provides limiting and locking possibilities over a clinically useful range.

5 Claims, 2 Drawing Sheets

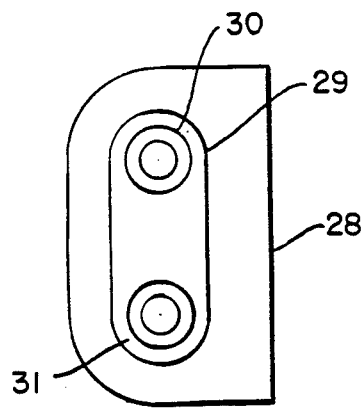
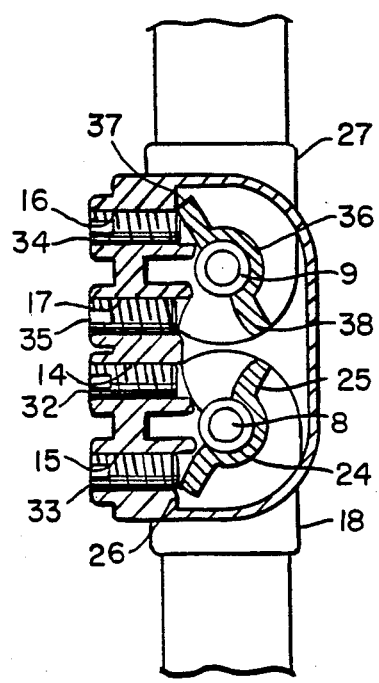
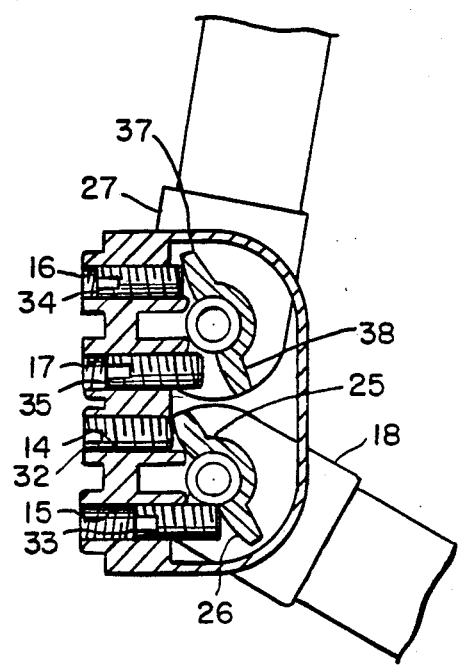

ORTHOPAEDIC HINGE MECHANISM

BACKGROUND OF THE INVENTION

1. Field of the Invention

The present invention relates generally to orthopaedic and orthotic hinge mechanisms which are used in braces of various kinds.

2. Introduction

Orthopaedic and orthotic hinges vary considerably in design and function. They are employed to cross joints, such as the knee or elbow and their function is usually to supplement or partially substitute for, the weight-bearing and motional characteristics of these joints. They are generally used in pairs with one hinge fitted laterally and the other fitted medially across the joint.

Orthopaedic and orthotic hinges are of two main types. The first employs a single pivot and is generally described as uniaxial or unipivotal; this type is quite commonly used in knee braces fitted in the practice of sports medicine often following damage to the ligaments of the knee.

Uniaxial hinges are very commonly fitted to heel cups which is the common name applied to the terminal element in a cast brace. More recently, uniaxial hinges have been used in lower leg walking devices for fractures of the foot: these are used instead of short leg walking casts.

The biomechanics of ankle motion are complex but the therapeutic requirements is normally to provide only plantarflexion/dorsiflexion; this is why uniaxial hinges can be used. In conditions such as ruptured Achilles tendon which has undergone surgical repair it is important to hold the foot in marked plantarflexion for part of the treatment period. This could be achieved with a device having a lockable uniaxial hinge.

Uniaxial hinges have also been used at the hip but when used alone they can only track the flexion/extension axis. Since the hip is a ball and socket joint capable of compound adductive/abductive motion and flexion-/extension motion i.e. circumduction, such hinges are clearly of limited value.

In biomechanical terms, single pivot hinges are unphysiological when used at the knee because the knee does not move as a simple pivot.

The second type of hinge mechanism is very widely used in cast bracing hinges and knee braces. In this type there is a central mount or plate which bears two pivots. The hinge arms are mounted, one on each pivot and each arm has gear teeth at its extreme end such that when mounted upon its pivot, the teeth mesh with that of its neighbour. The effect of this is that when one hinge arm is moved, the other hinge arm must move also.

In mechanical terms a geared two pivot mechanism loses one degree of freedom. Geared two pivot hinges are also unphysiological when used at the knee because they effectively offer a single pivot point which migrates backwards when the hinge is moved from the fully extended to the fully flexed condition. In commercially available types, this migration is about 8 mm.

Knee motion involves forward sliding of the femoral condyles over the tibial plateau as the knee extends from the fully flexed position. As the knee moves into the last 20 degrees or so of extension, a marked pivotal element is introduced and over the last 5 or so degrees of extension there is a rotational 'screwhome' component.

A third type of orthopaedic hinge does offer good tracking of the human knee joint by employing two truly independent pivots in conjunction with a stop incorporated in the hinge body to arrest uncontrolled anterior motion of the femoral condyles over the tibial plateau in a cruciate ligament deficient knee. This type of hinge is called a true bi-pivotal hinge or by some authors a true bi-axial hinge.

3. The Prior Art

Although several manufacturers employ single pivot hinges in heel cups these do not usually have adjusting or locking means.

Single pivot knee hinges are now used much less since uniaxial hinges cannot track the human knee satisfactorily. If the brace in which the hinge is incorporated fits snugly, the hinge will impart undesirable forces to the joint. Consequently, although the motion control mechanism Housewerth describes for a 'conventional' leg brace in U.S. Pat. No. 4,620,586 is clever and compact, the unfaxial hinge he uses is not suitable for physiological knee bracing applications.

A single pivot hinge is used in a knee brace supplied by Messrs Medical Designs Inc of Arlington, Tex., U.S.A. This design is disclosed in U.S. Pat. No. 4,489,718 to Martin and employs a slidable pivot and a stop peg limited by flexible plungers.

The hinge axis appears to be able to slide only about 7 mm, conferring only a minimal advantage is minimal since the instant centre pathway of the knee, during the sliding pase of flexion, can be shown to migrate considerably more than this and not in a straight line. The instant centre pathway of the knee is the locus of the effective knee axis as the knee joint moves through a complete cycle of flexion and extension.

The adjustment mechanism allows locking and limited ranges of motion. Long springs, carried within slots in one element of the hinge body, are driven by grub screws. A stop rivet which engages another element of the hinge body, extends into the slots occupied by the springs. Depending upon whether the springs are both driven up against the rivet or are parked some distance away from it, the hinge may be locked or allowed limited motion.

Although this adjustment mechanism is effective, the hinge body necessary to contain it confers a considerable weight and size penalty. The hinge body element containing the adjusters is about 4.25" long and about 1.75" wide, compared with 3.25" by 2.25" for another adjustable hinge body described below (Lerman) and 2.25" by 1.25" for the Protectair hinge also described below.

Commercially available geared two-pivot hinges have teeth around the edge of the pivot end of the hinge arm. Although each arm is pivoted separately in the hinge body, independent motion is prevented by mutual engagement of the gear teeth on each arm. The effect of this gearing mechanism is thus to reduce the motional capability of the hinge to a uniaxial device which flexes and extends about the point of engagement of the gear teeth, the hinge body moving posteriorly and anteriorly respectively, relative to said point of engagement.

Various embodiments of this basic hinge design allow controlled mobility and locking. For instance, in some types, a drop lock is used to fix the hinge in the fully extended position. This comprises a metal ring-piece fitted around one hinge arm. The ring can either be parked, away from the body of the hinge mechanism or it can be slid down the arm and over part of the hinge body is such a way that the arm is trapped. The ring can be locked in this latter position by means of a grub screw. By trapping the hinge arm against the body, all motion is prevented and the hinge becomes a straight strut.

In another variant, an arcuate slot in one part of the hinge body, lies over a tapped hole in one hinge arm. A threaded peg screws into the tapped hole in the hinge arm and acts as a stop. This arrangement gives the hinge a fixed limited range of motion determined by the angular dimension of the arcuate slot.

In U.S. Pat. No. 4,337,764 and published European Application No. 821015955 Lerman discloses an adjustment mechanism for two-pivot geared hinges. The system depends on a hinge backplate with an arcuate slot in which are located two compression screw sets lying outside either side of the hinge arm. In commercially available versions of this device, such as those hinges supplied in the USA by Messrs United States manufacturing Company of Pasadena, Calif., there are two such slots and a total of four compression screw sets.

Tests which we have carried out using an Instron machine, show that this mechanism is liable to slip at physiological loads and that this slippage occurs in an unpredictable manner.

In U.S. Pat. No. 4,599,998 to Castillo, a motion control system based on a ratchet mechanism is disclosed for geared two pivot hinges which is neat and compact but limited to that type of hinge only.

A different type of adjustment mechanism for a two-pivot geared hinge is used in a design supplied by Messrs Rolyan Manufacturing Co Inc of Menomonee Falls, Wis., U.S.A. In this device, two screws located in the top of the hinge body are used to limit travel of one hinge arm in flexion and extension respectively.

This is achieved by driving the screws down into the body so that the ends strike the top edges of the hinge arms. The screws remain exposed at all times and require a locking nut to maintain adjustment. The hinge may be free or locked in one position or set for limited ranges of motion.

We know of very few commercially available examples of true bipivotal hinges and we have found relatively few references in the art via patent searches.

We know of a sports brace made by Omni Scientific of Martinez, Calif. This is believed to be based on a patents granted to Anderson who has both a U.S. Pat. No. 4,249,524 and a PCT patent WO 82/02658.

Anderson teaches a bi-pivotal hinge in his US patent but we believe that this has unphysiological characteristics. This is because the pivots are very widely spaced and shortening could occur in the hinge as it flexes, leading to effective shortening of the cast or brace in which it is used. This allows the knee joint or limb to 'piston' which is undesirable, especially in a damaged knee or in a knee which has recently undergone surgical repair or in a leg where there is a fracture.

The hinge illustrated in Anderson's PCT patent, granted a year later than the US patent, is different insofar as the headplates are concerned but judging from the drawings he still discloses widely separated pivots.

In effect, the hinge centre bar in the US patent fulfils the function of both a mounting for the pivots and of hinge arms since it extends as far as the members normally regarded as headplates. In the PCT patent, so far as we can judge, the hinge centre bar appears to extend quite close to the headplates.

We believe that wide pivotal spacing is of significance in regard to 'pistoning' and will in addition detract from proper function of a hinge incorporated in a brace. For instance, where wide pivotal spacing is employed, the medial collateral ligament will receive little, if any, protection from the brace against a lateral blow when the knee is moderately flexed.

Although Anderson briefly mentions stops in his PCT patent he does not disclose a proper motion control system in any detail. In any such system, the interrelationship between the control of motion and the pivot spacing in true bi-pivotal hinges is important.

In 1983 we introduced into the European market, a true bi-pivotal hinge with closely spaced pivots. This is made by Messrs Protectair Limited of Stokenchurch, Buckinghamshire U.K. and is sold under the name Sheffield System. It features a hinge body with a metal chassis having arcuate slots at each end.

Compression screws, fitted with washers and nuts, lie in the slots and the positions of the compression screw sets may be varied over a wide range. Unlike the Lerman hinge, the compression screws do not act against either side of the hinge arms, instead they abut a pin rivetted to each hinge arm, centrally, under the arcuate slots. Like the Lerman hinge adjustment mechanism, this system has also been found on Instron testing, to slip at physiological loads. However, when accessory locking plates supplied for use with this design, were fitted, slippage was greatly reduced.

We have confirmed, by means of combined video, computer and force plate gait analysis, that our bi-pivotal knee hinges with closely spaced pivots introduce less disturbance to the normal gait (or walking pattern) than either geared two pivot hinges or single axis hinges.

Furthermore, we have confirmed at Sheffield and Brunel Universities, that with the spacing of the pivots we have used in bi-pivotal hinges, the instant centre pathway of the knee during the flexion/extension cycle can be almost entirely accommodated in the majority of adults.

Also, pistoning does not occur in such hinges as those immediately hereinbefore described when the knee is under load (provided the hinges are fitted properly).

Attention should be drawn to U.S. Pat. No. 4,520,802 granted to Mercer and Aaserude which teaches another bi-pivotal hinge featuring wide pivot spacing. These authors' principal disclosure is, however, their motion control system based on indexing blocks. The system they describe is discontinuous and leaves the user subject to the values on the index blocks made available by the manufacturer. In addition, the time taken to remove parts of the device and to select and substitute accessories would be considerable and not appropriate to busy clinics and doctors' offices where there is usually the need to process numerous patients efficiently and quickly. As taught, the intention seems primarily to provide flexion control.

Most hinges have securing means for fixing them directly or indirectly to a limb. Nowadays there is an increasing trend towards the use of devices which are retained on the limb by means of several straps. Where this method is employed, the hinge mechanism will usually have arms fitted with curved plates which are often called shells.

Where the hinge mechanism is to be retained on the limb by a cast, it will usually have hinge arms which terminate in structures adapted for embedding in the cast and frequently termed headplates or anchor plates.

Orthotic hinges are normally supplied as independent units which are subsequently either built directly onto plastic orthoses or fitted to mating side arms called 'steels' and incorporated into calipers. Lower limb orthoses in particular are generally secured to the limb with straps.

Observations made under widely varying conditions in several different countries lead us to the conclusion that strap-on devices, especially for the lower limb, almost always have more potential for relative motion between the limb and the device than do casts. This is primarily because casts are inherently rigid and constitute a fully circumferential integrated structural unit, whereas strap on devices are usually made from a combination of soft goods and flexible materials and cannot form an integrated circumferential structure.

It is important to understand, therefore, that in the design of motion control mechanisms for orthopaedic and orthotic hinges adjustments should be capable of continuous variation. This ensures that proper compensation for relative motion between the leg and the brace when such hinges are used with strap-on braces can be achieved.

Somewhat paradoxically, it is in the damaged but otherwise normal knee that the greatest attention to accurate tracking is necessary, since, with well managed rehabilitation, very good results can be obtained. However, with grossly damaged knees ravaged either by disease or birth defect and in which there is no hope of normal motion, a less complex hinge may often be used and other factors in the design of the device, such as locking mechanisms may be more important.

In published UK Pat. Application Number 2,163,352 and in U.S. Pat. Application No. 734,050 we disclosed a hip hinge capable of circumduction and of being locked in a number of abducted positions. We know of a single axis hip hinge formerly manufactured by Messrs Blatchfords of Basingstoke, UK and we have seen hinges according to Lerman modified for use as single axis hip hinges, thus providing a locking and limiting facility but on the flexion axis only.

AIMS OF THE INVENTION

It is a principal aim of the present invention to provide an orthopaedic hinge in which there is provided the facility for free motion plus locking facilities and adjustment means for securing limited ranges of motion continuously variable over a clinically useful range.

It is a another aim to provide an orthopaedic hinge with multiple adjustment facilities and which requires no additional accessories.

It is a further aim to provide an orthopaedic hinge wherein there is no risk of slippage or loss of adjustment at maximal physiological loads.

It is yet a further aim of the present invention to satisfy the foregoing aims in a versatile, convenient and compact manner.

BRIEF DESCRIPTION OF THE INVENTION

According to one aspect of the present invention, there is provided an orthopaedic hinge mechanism for use in braces, orthoses and other devices. The hinge has as its principal components, a hinge body which provides housing for motion limiting screws and a hinge pivot, motion limiting screws, a pivot, a backplate, a hinge arm carrier with a hole for accepting the pivot and cams lying either side of the pivot hole. A hinge arm or equivalent structure is mounted on the hinge arm carrier. When used as a knee hinge, two hinge units are built into one body; this version will first be summarised.

The hinge body is conveniently made in metal by casting or can be moulded in very strong composite material. It is more or less rectangular in plan, with rounded corners at each end of the lower long side. Two holes in the plan face of the hinge body accept inserts which are internally threaded, said inserts forming pivots or bearings for hinge arm carriers. The backplate is similar in under-plan outline to the hinge body. Holes in it line up with threaded holes in the pivot inserts and accept screws by means of which the backplate is secured to the hinge body.

The hinge arm carriers are made of metal and are more or less rectangular in plan with one end rounded. Near this end is a bearing hole which is a close fit over one insert. The other end is adapted to enable a hinge arm to be secured in place by a rivet or other convenient means. When assembled, the hinge body, backplate, hinge arm carriers and hinge arms are all in the same general plane.

The front face of the hinge body has four holes in it, each threaded throughout its length. Each hole is fitted with a socket screw the purpose of which is to limit hinge motion. The motion limiting screws lie in a plane at right angles to the axis of the pivot inserts as well as at right angles to the front face of the hinge.

On the plan face of each hinge arm carrier, close to and on either side of the bearing, abutment stops in the form of cams arise out of the main plane of the hinge. These cams thus have their striking or operating faces in the same plane as the axis of the pivot insert and at right angles to the plane of the hinge arm carrier.

Two motion limiting screws relate to each hinge arm carrier; one to limit extension, the other to limit flexion on each hinge arm respectively. Limitation of motion is achieved by driving the screws down until they impinge upon their respective cams at the desired stop position.

If the motion limiting screws are not driven down, the hinge motion is unrestricted.

If the motion limiting screws are partially driven down, limited arcs of motion are imposed on the hinge arms.

If the motion limiting screws relating to one hinge arm are both driven against the stops, the arm will be locked.

If the motion limiting screws relating to both hinge arms are driven against the stops, the whole hinge will be locked.

This arrangement is a deadstop mechanism and unlike motion limiting mechanisms of prior art two-pivot knee hinges such as the geared hinges taught by Lerman or true bi-pivotal hinges such as our own Sheffield System, the instant invention has been shown to withstand slippage at loads well above the physiological maximum.

Goniometer markings are provided on the plan surface of the hinge body so that where conditions such as locking at a fixed angle or limited arcs of motion are required, these can easily be set up and checked simply by using the vernier drive of the motion limiting screws to position the stops at the required angles.

By appropriate sizing of the hinge body and arm carriers, motion limiting screws can be selected which neither protrude from the hinge body when the hinge is allowed free motion, nor fall through into the enclosed part of the assembly even when screwed right down.

BRIEF DESCRIPTION OF THE DRAWINGS

In order that the invention may be more clearly understood, reference will now be made to the accompanying drawings in which:

FIG. 3 is an underplan view of the backplate.

FIG. 4 is a front sectional view of the assembled bi-pivotal hinge mechanism with the motion limiting screws retracted to allow unrestricted motion of both first and second hinge arms.

FIG. 5 is a front sectional view of the assembled bi-pivotal hinge mechanism of FIG. 4, with the limiting screws locking the first hinge arm at full flexion and set to impose a 20 degree range of motion between 10 and 30 degrees of flexion on the second hinge arm.

DETAILED DESCRIPTION OF THE PREFERRED EMBODIMENTS

Orthopaedic hinge mechanisms are incorporated in braces and orthoses used at various joints. Accordingly, a series of embodiments which are generally preferred embodiments, will be described for use at different joints.

Thus in FIGS. 1-5, there are shown various aspects of a preferred embodiment of an orthopaedic hinge mechanism for the knee which has true bi-pivotal characteristics: this is to say that the hinge features two independent pivots.

Figure 1:
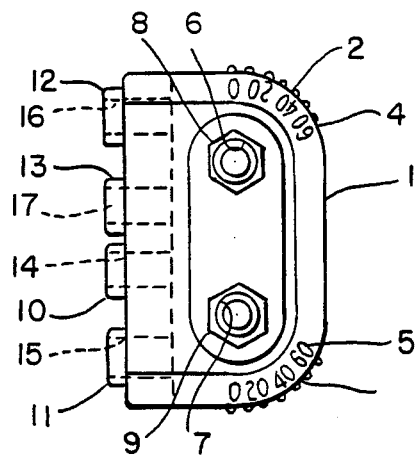
FIG. 1 is a plan view of the hinge body of a preferred true bi-pivotal embodiment.

Referring first to FIG. 1, a hinge body 1, is conveniently made in metal by casting or in suitable strong composite material by moulding. Corners 2 and 3, are rounded and have engraved goniometer markings 4 and 5, adjacent. Holes 6 and 7, are so sized and recessed as to accept hexagon headed, threaded inserts 8 and 9, which constitute first and second pivots. Bosses 10, 11, 12 and 13, have first, second, third and fourth threaded holes 14, 15, 16 and 17, shown in hidden detail.

Figure 2A:
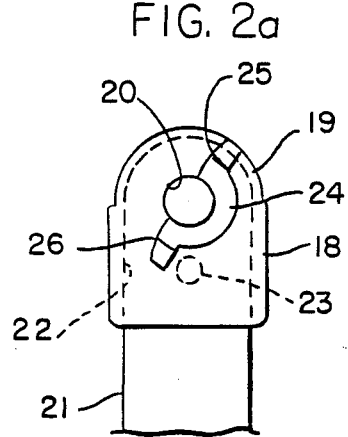
FIG. 2a and 2b are plan views of the first and second hinge arm carriers relating to the embodiment of FIG. 1 above.

In FIG. 2a, there is shown a first hinge arm carrier 18, rounded at one end 19 and conveniently made in metal by casting. A hole 20, near the rounded end acts as a bearing. A first hinge arm 21, fits intimately into a slot 22, formed in the outer end of first hinge arm carrier 18 and is retained in place by a rivet 23, shown in hidden detail. An anterior raised portion 24, of first hinge arm carrier 18, extends around either side of hole 20, providing first and second cam abutment stops 25 and 26.

Figure 2B:
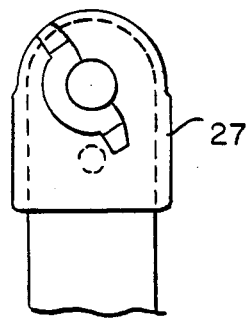

Second hinge arm carrier 27, of FIG. 2b, is a mirror image of the first hinge arm carrier 18 but is in all other respects identical.

In FIG. 3, there is shown a backplate 28, which conforms in general external outline to hinge body 1, of FIG. 1. A raised central portion 29, has countersunk holes 30 and 31, which accept screws (not shown) to attach backplate 28, to hinge body 1, of FIG. 1.

In FIG. 4, there is shown a front sectional view of the assembled bi-pivotal hinge mechanism. It can now be seen that first and second hinge arm carriers 18 and 27, are borne on inserts 8 and 9, previously described in FIG. 1, which act as first and second pivots. Socket screws 32, 33, 34 and 35 constitute first, second, third and fourth motion limiting screws and are located within first, second, third and fourth threaded holes 14, 15, 16 and 17, respectively.

Anterior raised portion 24, of first hinge arm carrier 18, extends around either side of pivot 8 and forms first and second cam abutment stops 25 and 26, which lie under first and second motion limiting screws 32 and 33, respectively. Corresponding anterior raised portion 36, of second hinge arm carrier 27, extends around either side of pivot 9 and forms third and fourth cam abutment stops 37 and 38, which lie under third and fourth motion limiting screws 34 and 35, respectively. First, second, third and fourth cam abutment stops 25, 26, 37 and 38, all have operating surfaces which lie in a plane at right angles to the axis of limiting screws 32, 33, 34 and 35 and also lie in a plane at right angles to the plane of hinge arm carriers 18 and 27.

FIG. 4, represents the condition where the hinge is set for a full range of free motion. First, second, third and fourth motion limiting screws 32, 33, 34 and 35 are retracted completely into holes 14, 15, 16 and 17, respectively and only the metal of hinge body 1, limits travel of first and second hinge arm carriers 18 and 27, at the full extent of the range of motion of the hinge.

In FIG. 5, two other representative conditions are shown. First hinge arm carrier 18, is locked at full flexion by driving the second motion limiting (extension blocking) screw 33, down second threaded hole 15, against the surface of second cam abutment stop 26, such that first cam abutment stop 25, is driven against the hinge body 1, at the lower end of hole 14, deadlocking the mechanism. First motion limiting (flexion blocking) screw 32, has been driven down first threaded hole 14, to meet the surface of first cam abutment stop 25.

Also in FIG. 5, second hinge arm carrier 27, is allowed 20 degrees of motion between 10 degrees flexion and 30 degrees flexion. This is achieved by driving third motion limiting (extension blocking) screw 34, down third threaded hole 16, until second hinge arm carrier 27, cannot pass below 10 degrees of flexion due to contact between the surface of third cam abutment stop 37 and said third motion limiting screw 34. Additionally, fourth motion limiting (flexion blocking) screw 35, is driven down fourth threaded hole 17, until it strikes the surface of fourth cam abutment stop 38, when second hinge arm carrier 27, is flexed to the 30 degree position.

The preferred embodiment of a bi-pivotal knee hinge immediately hereinbefore described is compact and very strong. The mechanism has been subjected to testing on an Instron machine at loads greatly above those which are possible in clinical use without any demonstrable slippage. This was in marked contradistinction to both geared hinges according to Lerman and to our own Sheffield System hinges. Prolonged series of cyclic stress reversal tests at high loads have been conducted which have demonstrated excellent durability. Hinges according to the preferred embodiment are intended to be used in pairs, one either side of the knee.

In all the preferred embodiments the preferred motion limiting screw is of the socket type with a fine pitch. In the preferred embodiments there is never less than half the threaded length of the motion limiting screw in engagement with the hole, hence the load transmitted from each of the abutment stops to the screws is never distributed over a thread length of less than:

$$\pi \times D \times L$$

where $D$, is the diameter of the screw and $L$, is the length of the screw engaged with the hole. For example where a 6 mm diameter screw with a pitch of 1 mm is used and 8 turns remain engaged with the hole when the screw is fully deployed, the minimum thread length engaged is 150.9 mm.

From the description of the preferred embodiments, it will be clear that many variations of the invention may be made according to the principles disclosed therein.

What is now claimed as new is:

1. An orthopaedic and orthotic hinge mechanism comprising a hinge body; a first hinge arm having one end thereof pivotally connected to said body for flexion and extension of said arm in a plane of movement about a first pivot axis; said body having a first pair of threaded holes extending along said plane of movement on opposite sides of, and at generally right angles to, said pivot axis; said first hinge arm including an anterior raised portion having one end providing one of a first pair of abutment stops and having a second end providing the other one of said first pair of abutment stops; said first pair of abutment stops being adjacent to said first pivot axis on opposite sides thereof; said first and second adjustment screws threadedly received in said first pair of holes for engaging said first pair of abutment stops and for selectively and adjustably controlling flexion and extension of said first hinge arm in a continuously variable manner over a clinically useful range; said first pair of threaded holes being located along one side of said body; a second hinge arm is pivotally connected to said body for movement about a second pivot axis; said body having a second pair of threaded holes extending on opposite sides of, and at generally right angles to, said second pivot axis; said second hinge arm providing a second pair of abutment stops adjacent to said second pivot axis and on opposite sides thereof; and third and fourth adjustment screws threadedly received in said second pair of holes for engaging said second pair of abutment stops and for selectively and adjustably controlling flexion and extension of said second hinge arm in a continuously variable manner over a clinically useful range.

2. The hinge mechanism of claim 1 in which said threaded holes of said first pair are parallel with each other.

3. The hinge mechanism of claim 1 in which said threaded holes of first and second pairs of threaded holes are parallel with each other and are located along the same side of said hinge body.

4. The hinge mechanism of claim 1 in which said first and second pivot axes are parallel to each other and said first and second hinge arms are supported for pivotal movement in substantially the same plane.

5. The hinge mechanism of claim 4 in which said first and second hinge arms are mounted for independent pivotal movement about said first and second pivot axes.

* * * * *